United States Patent
Natarajan et al.

(10) Patent No.: US 10,667,690 B2
(45) Date of Patent: Jun. 2, 2020

(54) COMPRESSIVE SENSING SPARSE SAMPLING PHOTOPLETHYSMOGRAM (PPG) MEASUREMENT

(71) Applicant: Intel Corporation, Santa Clara, CA (US)

(72) Inventors: Venkat Natarajan, Bangalore (IN); Deeksha Dadhich, Nashik (IN); Kumar Ranganathan, Bangalore (IN)

(73) Assignee: Intel Corporation, Santa Clara, CA (US)

( * ) Notice: Subject to any disclaimer, the term of this patent is extended or adjusted under 35 U.S.C. 154(b) by 730 days.

(21) Appl. No.: 15/089,501

(22) Filed: Apr. 2, 2016

(65) Prior Publication Data

US 2017/0281013 A1    Oct. 5, 2017

(51) Int. Cl.
*A61B 5/1455* (2006.01)
*A61B 5/00* (2006.01)

(52) U.S. Cl.
CPC .......... *A61B 5/002* (2013.01); *A61B 5/14551* (2013.01); *A61B 5/7225* (2013.01); *A61B 5/6802* (2013.01); *A61B 5/7257* (2013.01); *A61B 2560/0204* (2013.01)

(58) Field of Classification Search
CPC . A61B 5/0205; A61B 5/1455; A61B 5/14551; A61B 5/14552; A61B 5/72; A61B 5/7257; A61B 5/7225; A61B 5/742; A61B 5/002; A61B 5/6804
See application file for complete search history.

(56) References Cited

U.S. PATENT DOCUMENTS

| | | |
|---|---|---|
| 4,846,183 A | 7/1989 | Martin |
| 6,697,655 B2 | 2/2004 | Sueppel et al. |
| 2006/0211930 A1 | 9/2006 | Scharf et al. |
| 2010/0082302 A1* | 4/2010 | Garudadri ............ A61B 5/0006 702/189 |
| 2012/0250748 A1 | 10/2012 | Nguyen et al. |
| 2013/0114872 A1 | 5/2013 | Chen et al. |
| 2014/0046208 A1 | 2/2014 | Sejdic et al. |
| 2014/0214330 A1* | 7/2014 | Iyer ...................... A61B 5/7203 702/19 |
| 2015/0002852 A1 | 1/2015 | Groot et al. |
| 2015/0018647 A1 | 1/2015 | Mandel et al. |

(Continued)

FOREIGN PATENT DOCUMENTS

WO    2015159187 A1    10/2015

OTHER PUBLICATIONS

Emmanuel Candes and Justin Romberg, Sparsity and Incoherence in Compressive Sampling, Nov. 2006, 20 pages.

(Continued)

*Primary Examiner* — Eric F Winakur
*Assistant Examiner* — Chu Chuan Liu
(74) *Attorney, Agent, or Firm* — Compass IP Law PC

(57) ABSTRACT

A photoplethysmogram (PPG) measurement includes the use of compressive sensing based on samples generated in accordance with a fixed pattern. A pulse oximeter circuit can drive an LED according to the fixed pattern to create a compressive sensing sample matrix of sparse measurements. The fixed pattern can be a binary progression. The PPG signal reconstruction can include zero padding the sample matrix.

20 Claims, 9 Drawing Sheets

(56) References Cited

U.S. PATENT DOCUMENTS

2015/0204981 A1\* 7/2015 Kong ................ G01S 19/24
                                                    342/357.63
2016/0187446 A1   6/2016 Zhou et al.

OTHER PUBLICATIONS

Mohamed Elgendi, On the Analysis of Fingertip Photoplethysmogram Signals, 2012 Bentham Science Publishers, current Cardiology Reviews, 2012, 8, 14-25, Revised: Apr. 12, 2012, Accepted: Apr. 13, 2012, 12 pages.

Mohamed Elgendi, Standard Terminologies for Photoplethysmogram Signals, Research Gate, Article in Current Cardiology Reviews—Jun. 2012, Current Cardiology Reviews, 2012, 8, 215-219, 2012 Bentham Science Publishers, 6 pages.

Pawan K. Baheti and Harinath Garudadri, An ultra low power pulse oximeter sensor based on compressed sensing, 2009 Body Sensor Networks, pp. 144-148, 2009 IEEE, 5 pages.

Sagar Venkatesh Gubbi and Bharadwaj Amrutur, Senior Member, IEEE, Adaptive Pulse Width Control and Sampling for Low Power Pulse Oximetry, IEEE Transactions on Biomedical Circuits and Systems, This article has been accepted for inclusion in a future issue of this journal. Content is final as presented, with the axception of pagination.12 pages.

International Search Report and Written Opinion for PCT Patent Application No. PCT/US2017/021006, dated May 30, 2017, 14 pages.

\* cited by examiner

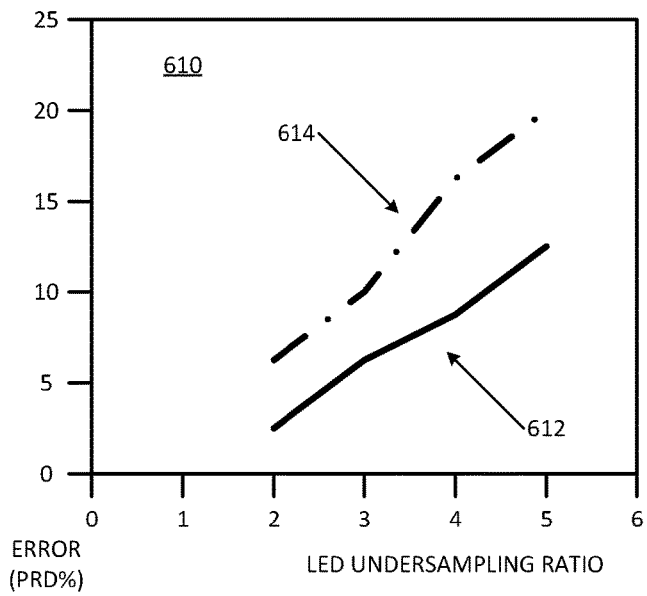
FIG. 6A
TABLE 620
| RECON-STRUCTED PPG FREQ (Hz) | CS LED SAMPLES REQ/SEC | HR ERROR % | TRADI-TIONAL SAMPLES REQ/SEC |
|---|---|---|---|
| 32 | 6 | 2 | 12 |
| 100 | 11 | 2 | 22 |
FIG. 6B
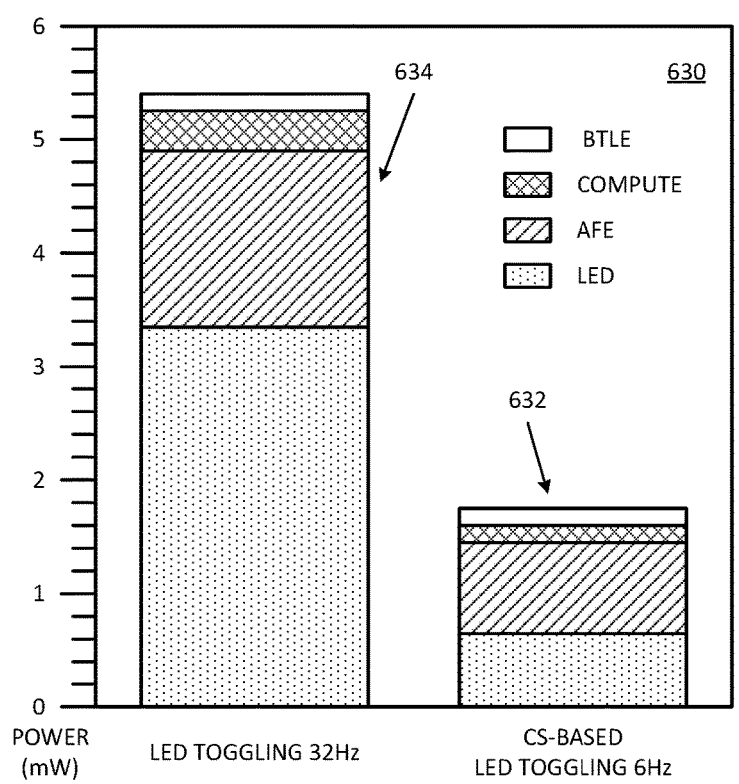
FIG. 6C
TABLE 640
| SUB-SYSTEM | POWER SAVINGS % |
|---|---|
| LED | 80.4 |
| AFE | 48.7 |
| LED | 59.8 |
| BTLE | - |
| TOTAL | 68 |
FIG. 6D

COMPRESSIVE SENSING SPARSE SAMPLING PHOTOPLETHYSMOGRAM (PPG) MEASUREMENT

FIELD

The descriptions are generally related to sensor devices, and more particular descriptions are related to a wearable PPG (photoplethysmogram) system that operates based on compressive sensing sparse sampling.

COPYRIGHT NOTICE/PERMISSION

Portions of the disclosure of this patent document may contain material that is subject to copyright protection. The copyright owner has no objection to the reproduction by anyone of the patent document or the patent disclosure as it appears in the Patent and Trademark Office patent file or records, but otherwise reserves all copyright rights whatsoever. The copyright notice applies to all data as described below, and in the accompanying drawings hereto, as well as to any software described below: Copyright © 2016, Intel Corporation, All Rights Reserved.

BACKGROUND

Advances in computing technologies and sensor devices encourages the incorporation of more technology in wearable sensors and personal computing systems. Such technologies offer the hope of obtaining reasonably accurate biometric data from devices that are small and unobtrusive enough to be carried and/or worn. Biometric data has particular interest in health and well-being monitoring, as well as sports performance monitoring. Biometric data is also useful for identity verification, such as data to implement two-factor authentication. However, there are traditionally many limitations encountered in designing and implementing actual systems that generate usable biometric data.

For example, a pulse oximeter is a device that measures a plethysmogram using an optical pulse, or a photoplethysmogram (PPG). A pulse oximeter pulses an LED (light emitting diode) to measure blood pulsation. The blood pulsation offers a good heart rate measurement alternative to an electrocardiogram (or electrokardiogram (EKG)). A pulse oximeter can also provide a blood pressure estimate, as well as a blood oxygen saturation level estimate. Thus, continuous PPG signal sensing in a wearable sensor can enable realtime monitoring of heartrate, blood pressure, and/or oxygen saturation in free-living conditions. Free living conditions refer to the real life scenarios encountered as a subject goes about his or her activities, instead of only obtaining measurements in controlled environments. PPG signal sensing in a non-continuous manner does not offer the information available from continuous monitoring.

However, traditional approaches to designing wearable pulse oximeters result in systems with power consumption requirements that result in poor battery life. With such traditional approaches, there is a tradeoff between extending battery life and recovering an accurate PPG signal. Typically, techniques to extend the battery life sacrifice PPG signal accuracy, and attempts to obtain better PPG signal accuracy leads to battery drain that makes PPG unsuitable for continuous sensing over a prolonged period. The LED pulsing consumes approximately 80% of system power in a conventional 32 Hz PPG design.

Thus, traditional PPG systems that run continuously at 32 Hz have unacceptable battery life. One proposal to save power is to sample at a lower rate with an intelligent sampling algorithm. However, traditional intelligent sampling algorithms require the use of an on-board random number generator, and therefore consume considerable power. Intelligent sampling saves LED power, but increases other power usage, which limits the amount of overall system power saved. The result is a system that still has poor battery performance.

BRIEF DESCRIPTION OF THE DRAWINGS

The following description includes discussion of figures having illustrations given by way of example of implementations of embodiments of the invention. The drawings should be understood by way of example, and not by way of limitation. As used herein, references to one or more "embodiments" are to be understood as describing a particular feature, structure, and/or characteristic included in at least one implementation of the invention. Thus, phrases such as "in one embodiment" or "in an alternate embodiment" appearing herein describe various embodiments and implementations of the invention, and do not necessarily all refer to the same embodiment. However, they are also not necessarily mutually exclusive.

FIGS. 6A-6D are diagrammatic representations of power savings obtained by a PPG measurement system in accordance with an embodiment of compressive sensing PPG signal reconstruction.

Figure 1:
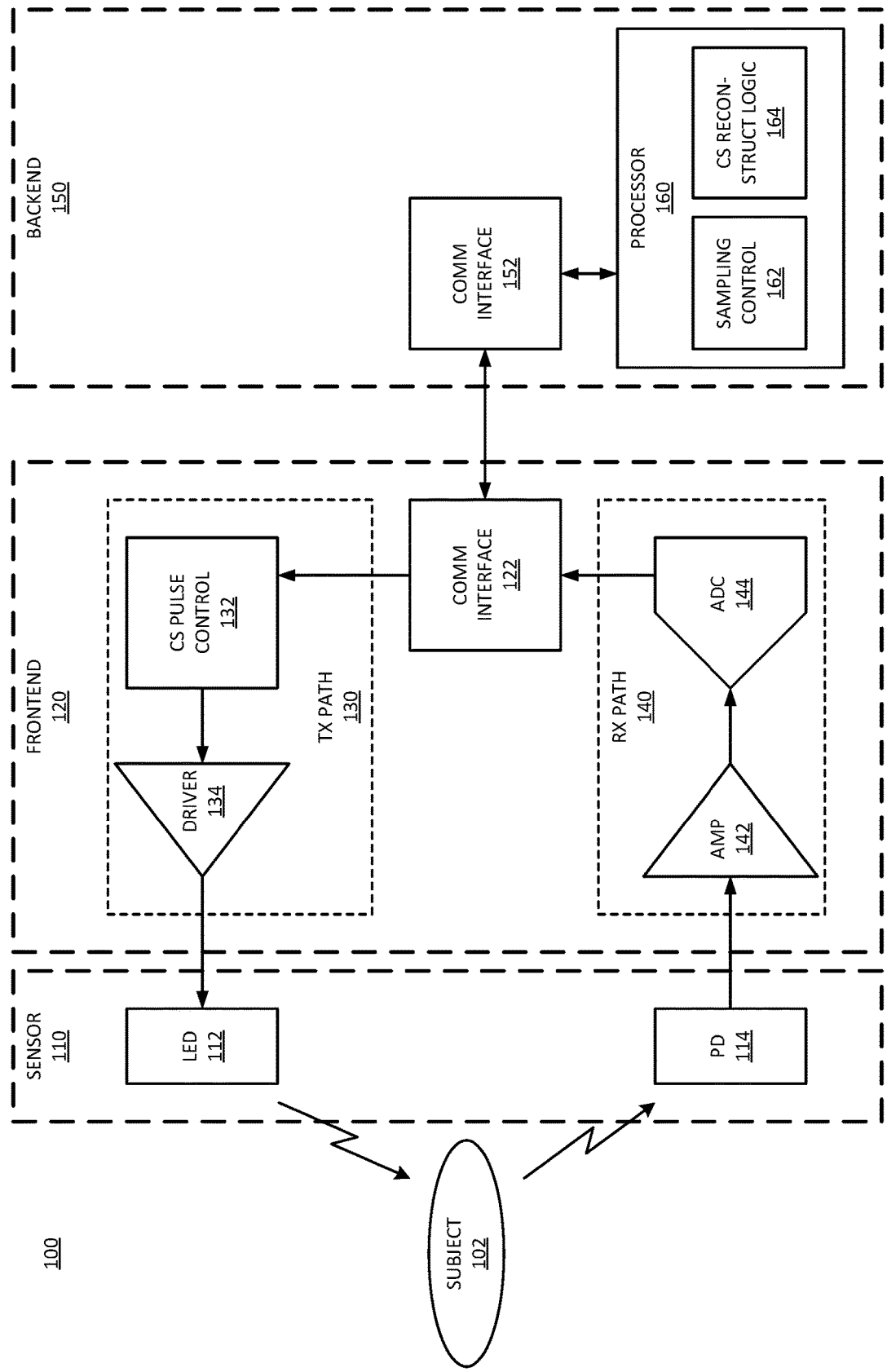
FIG. 1 is a block diagram of an embodiment of a system with a PPG system that performs sampling and PPG signal reconstruction based on a sparse measurement pattern.

Descriptions of certain details and implementations follow, including a description of the figures, which may depict some or all of the embodiments described below, as well as discussing other potential embodiments or implementations of the inventive concepts presented herein.

DETAILED DESCRIPTION

As described herein, a pulse oximeter system generates photoplethysmogram (PPG) signal samples in accordance with a fixed pattern. The pulse oximeter system applies compressive sensing based on a sparse matrix of the samples generated. Compressive sensing refers to data compression in a sampling system, where an input signal is subsampled with sufficient data to perform signal recovery with acceptable accuracy. Subsampling refers to sampling an input signal at lower than the Nyquist rate. It will be understood that the Nyquist rate refers to a sampling rate for sampling an input signal at a frequency of at least twice the frequency of data desired to be recovered. With Nyquist sampling, a system can reconstruct a signal with minimal loss below the frequency of the data desired to be recovered.

Compressive sensing can provide highly power-efficient sampling and reconstruction by toggling the LED (light emitting diode) of the pulse oximeter at a rate slower than the traditional 32 Hz continuous sampling. Based on the use of compressive sensing, a pulse oximeter system can subsample PPG measurements and recover a 32 Hz PPG signal. More specifically, in one embodiment, a pulse oximeter circuit can drive an LED according to a fixed pattern to create a compressive sensing sample matrix of sparse measurements. In one embodiment, the pulse oximeter system is separated into separate sensor and processor elements, and the compressive sensing can control the power efficiency of the sensor.

Traditional PPG measurement involves the use of continuous sampling. One approach designed to save power compared to continuous sampling involves the use of random sampling. A random sampling matrix can satisfy sufficient mathematical properties of compressive sensing to enable signal recovery. However, random sampling is not a good match for wearable devices. Random sampling requires an on-board random number generator at the sensor, which has a lot of inefficiency and consumes significant amounts of power. As described herein, a pulse oximeter system can apply a fixed sampling schedule for compressive sensing reconstruction of the PPG signal. In one embodiment, the pulse oximeter circuit generates PPG measurement samples in accordance with a toggling schedule that exploits the inherent sparsity in a PPG signal.

The toggling schedule or toggling sequence or pattern refers to a series of pulses by the LED of the pulse oximeter. It will be understood that the photodetector detects light interference with the target in response to the pulse of light by the LED. Reference to interference with the target or interfering with the target refers to the fact that light from the LED will be absorbed and/or scattered by the subject, and light detection at the photodetector can measure how much light from the LED light pulse reaches the photodetector. Thus, the photodetector generates measurements that represent samples of PPG information. Based on the pulsation of blood through the subject's tissue, the light detection will vary even from the same LED pulse output. Thus, consistent power output from the LED on each pulse will result in different light detection at the photodetector based on different interference with the subject because of blood pulsation. The light detection can therefore represent a sampling sequence corresponding to the toggling sequence. The photodetector measurements provide data for a sparse measurement or sample matrix from which the system can compute a PPG signal reconstruction.

In one embodiment, the sampling sequence is in accordance with a power law. For example, in one embodiment, the pulse oximeter pulses the LED on a binary progression schedule, which generates a sample matrix with measurements spaced in accordance with a binary geometric progression. The use of the binary sequence generates the fewest number of samples possible. The binary sequence provides a fixed pattern with low sample coherence, and without requiring the use of a random number generator. While a binary sequence is discussed herein, it will be understood that another fixed sequence could alternatively be used that does not require random number generation, and that also satisfies the mathematical properties for compressive sensing. It is believed that a binary sequence provides the sparsest sample matrix, but a sample matrix that is less sparse could also save significant power over the traditional methods used. Thus, the binary sequence will be understood as a non-limiting example. In general the pulse oximeter system generates sparse samples based on a fixed schedule for compressive sensing reconstruction.

In one embodiment, the fixed schedule is a binary progression in accordance with $2^i$, where i is the sample number $\{0, 1, 2, \ldots\}$. In addition to satisfying the properties of compressive sensing, such a sampling sequence provides improved recovery. In one embodiment, the compressive sensing signal recovery or reconstruction performs computations based on a discrete transform sparse basis representation, such as a discrete Fourier transform representation, a discrete cosine transform, or other transform. The binary pattern in the sample matrix enables a binary-based recovery in the frequency domain. In one embodiment, the PPG signal reconstruction processing can include zero padding the sample matrix. More detail of zero padding is provided below, but briefly, the zero padding provides a more accurate recovery at the expense of more processing. However, the simplification of a binary-based frequency domain recovery can justify the additional processing from the zero padding.

The pulse oximeter based on a fixed sequence sparse sample matrix for compressive sensing PPG signal recovery provides an architecture suited for PPG monitoring in on the go or free living systems. The sparse sampling significantly reduces the sampling requirements, and saves enough power to prevent draining the battery too fast. In one embodiment, the architecture includes a separation of the wearable sensor that generates the measurement samples and the computing or processing element that performs signal recovery. The two elements can be combined via wired and/or wireless communication. Such an architecture can provide a simple sensing node that can be implemented on a system on a chip (SOC) design. The SOC can interconnect with a local or remote processor to perform signal processing on the samples.

FIG. 1 is a block diagram of an embodiment of a system with a PPG system that performs sampling and PPG signal reconstruction based on a sparse measurement pattern. System 100 provides one example of a pulse oximeter or a PPG monitoring system. Subject 102 represents a human target of the PPG monitoring. System 100 can monitor by pulsing LED light on subject 102 and measuring light from the subject in a photodetector.

System 100 includes sensor component 110, which includes one or more LEDs 112 and one or more photodetectors (PDs) 114. It will be understood that LED 112 can represent different types of LED that emit different types of light, depending on the application of system 100. For example, for certain systems, LED 112 emits green light that will be reflected off of subject 102. Thus, PD 114 could detect reflected light. In another example, LED 112 can emit red and/or infrared light that will penetrate the skin of subject 102. Thus, PD 114 could detect light that penetrates through subject 102. Either the scattering off the surface of subject 102 or the penetration of light through 102 can be referred to as interference of the light pulses with subject 102. If there are multiple LEDs 112, the LEDs can be of different types from each other. Different PD types can also be used to complement different LED types, depending on the implementation of system 100.

Sensor 110 represents hardware components that interface directly with subject 102. Frontend 120 represents a circuit or SOC components that drive LED 112 and receive the input signals from PD 114. Frontend 120 can be referred to as an analog frontend or AFE, in one embodiment. Frontend 120 can be referred to as an interface circuit, referring to the interfacing of the sensors with backend 150 or other processing unit. In one embodiment, frontend 120 includes transmit (TX) path 130 and receive (RX) path 140.

In one embodiment, TX path 130 includes pulse control 132, which specifically refers to pulse control circuitry and/or logic that causes LED 112 to emit light pulses in accordance with a pattern for compressive sensing (CS) reconstruction. In one embodiment, pulse control 132 includes logic and/or storage on frontend 120 necessary to perform the pulse scheduling. In one embodiment, pulse control 132 receives data and/or commands from backend 150 via communication (comm) interface 122. For example, the backend may provide the pulse sequence to pulse control 132 in one implementation. TX path 130 includes driver 134 to generate the voltage and/or current necessary to cause LED 112 to emit its light. Pulse control 132 causes driver 134 to operate to pulse LED 112 in accordance with a fixed pattern for PPG measurement.

In one embodiment, RX path 140 includes amplifier (amp) 142 to receive and amplify an analog signal from PD 114. When PD 114 detects light, it generates an output. Typically PD 114 outputs a signal that varies in current based on the intensity of light received at the detector. Thus, amplifier 142 can typically be or include a transimpedance amplifier (TIA) that converts an input signal that varies in current output into a signal that varies in voltage level. In one embodiment, RX path 140 includes analog to digital converter (ADC) 144, which can convert an analog signal into a digital representation (1s and 0s representation). In one embodiment, ADC 144 converts the output of amplifier 142 into a digital representation. The digital samples can be considered data points or measurement data for signal recovery.

With sensor devices, it is common to make a distinction between a "raw" signal or "raw data," and data that is not "raw." Raw data refers to data that is a pure representation of a measurement. Raw data can thus refer to the actual analog voltage and/or current level generated by a sensor device or sensor circuit. However, raw data can also refer to a digital representation of that data, if the analog version is simply converted into a digital representation of the measurement. It will be understood that processors or controllers cannot process analog signals, but use a binary digital representation for computations. Thus, while signals that are converted into a digital representation could from one perspective be considered to be processed in the sense that circuit equipment operated on the data to convert it to digital form, it is common to still think of data as raw that has only been converted to digital representation. Data that is not raw has been interpreted or interpolated through some computation or processing, and is a representation of something other than pure measurement data.

In one embodiment, frontend 120 provides raw measurement data to backend 150 for processing. While not specifically shown in system 100, frontend 120 includes a buffer or storage to store a series of measurement data. The implementation of system 100 will determine the size of the measurement buffer. In one embodiment, frontend 120 stores only measurements, which can then be interpreted for timing by backend 150. Thus, in an implementation where pulse control 132 causes LED 112 via driver 134 to generate pulses separated in time by a binary geometric progression, PD 114 can measure a reflection from each pulse generated by LED 112, which can then be converted to a digital representation by amplifier 142 and ADC 144. Each digital measurement can be stored in a subsequent buffer entry, even if separated by differing amounts of time between samples. Backend 150 knows the sampling pattern used by frontend 120 and sensor 110, and can perform computations knowing the timing of each successive sample of the series of samples.

In one embodiment, backend 150 interfaces with frontend 120 via communication interface 152, which communicatively couples to communication interface 122. Communicative coupling refers to exchanging of information between the components over a communication link. In one embodiment, the communication link includes a wired connection. In one embodiment, the communication link includes a wireless connection. In one embodiment, communication interface 122 is or includes a transmitter or a transceiver or other communication circuit. In one embodiment, communication interface 122 is or includes a radio circuit, which generates a wireless signal to corresponding communication interface 152. Such a radio circuit could include, for example, a Bluetooth signal or other RF (radio frequency) signal.

In one embodiment, backend 150 is a separate physical devices from a device that houses frontend 120 and sensor 110. For example, in one embodiment, frontend 120 and sensor 110 are implemented on an SOC that straps to a wrist, arm, chest, or other portion of subject 102 with LED 112 and PD 114 facing the subject's skin. Backend 150 can include processing equipment in another device, such as a watch, phone, or other processing unit or device with a processing unit. Such a processing unit can be part of a personal area network of subject 102. In one embodiment, sensor 110 generates measurement information, which frontend 120 buffers and sends to backend 150. Backend 150 can then process the measurement information to extract PPG signal information.

Pulse control 132 non-uniformly toggles one or more LEDs 112 via driver 134. In one embodiment, LED 112 pulses at approximately 5-6 Hz on average, from which PD 114 and RX path 140 generate corresponding measurements. Based on the 5-6 Hz pulsation of LED 112, system 100 applies compressive sensing reconstruction at processor 160 to recover the PPG signal as if it ware sampled at 32 Hz. However, rather than using as much power as a traditional system that monitors continuously at 32 Hz (e.g., a fixed schedule for pulsing the LED that generates 32 samples per second), LED power consumption for system 100 is correspondingly reduced and the overall system power consumption of the edge-node (e.g., frontend 120 and sensor 110) can be reduced by approximately 68%, as described in more detail below with respect to FIGS. 6A-6D. It will be understood that with fewer measurements in system 100 relative to a traditional system, transmission power for communication interface 122 can be reduces by approximately 5× (e.g., 5 to 6 samples instead of 32 samples).

Backend 150 includes processor 160, which is illustrated as including sampling control 162 and CS reconstruction logic 164. Processor 160 can be or include any type of processing unit to perform reconstruction computations. In one embodiment, processor 160 includes a digital signal processor. In one embodiment, processor 160 includes a microcontroller. In one embodiment, processor 160 includes a central processing unit. Processor 160 can be part of a dedicated processing device, or the processor of a multipurpose or general purpose device.

Sampling control 162 represents logic within processor 160 and/or another component of backend 150 that knows the sampling schedule for sensor 110. In one embodiment, sampling control 162 can provide one or more commands or signals to frontend 120 to enable the frontend to drive sensor 110 in accordance with the schedule. In one embodiment, sampling control 162 merely represents knowledge at the processor of the sampling schedule, which enables processor 160 to compute a PPG signal from measurements received from frontend 120.

Reconstruction logic 164 represents logic within processor 160 to perform PPG signal recovery from the received samples. In one embodiment, frontend 120 generates and sends a series of measurements to backend 150. Even as a series of samples, when the sampling schedule is known, the series of measurements indicated by the samples represents a sparse measurement matrix. Thus, while a matrix used for PPG signal reconstruction will necessarily include zeros in areas not populated in accordance with the sparse sampling (e.g., each bin of the 32 Hz signal for which there is no measurement data), the data transmitted by frontend 120 can be considered the sampling matrix. In one embodiment, there is not considered to be any matrix until processor 160 (or another component of backend 150) generates a matrix from the received sample data, such as by representing the measurement data as a sparse measurement matrix based on the sampling schedule.

In one embodiment, system 100 is implemented with a computationally weak but energy efficient sensor node that includes sensor 100 and frontend 120, and a computationally stronger processor node that includes backend 150. The sensor node generates measurements for compressive sensing reconstructions. The processor node recovers the original signal completely, and is not necessarily designed to be as low power as the sensor node. Typically, the processor node or gateway device will include a larger battery. In one embodiment, reconstruction logic 164 implements CS-based signal reconstruction algorithms. In one embodiment, the sensor node implements a non-uniform toggling measurement sequence in the time-domain and processor 160 reconstructs the PPG signal information in a sparse Fourier basis via CS-based signal reconstruction algorithms with reconstruction logic 164. When the sensor node captures measurements with time intervals between samples based on a powers of 2 sequence, system 100 requires fewer samples than other techniques. System 100 can even implement a signal recovery with approximately ¼ to ½ the number of samples required by other standard compressive sensing sampling encoding schemes, such as random sampling. In one embodiment, system 100 applies the same LED toggling/sampling pattern or schedule across all sampling windows. Such fixed pattern sampling is in contrast to dynamically varying the sampling for each window with special embedded logic as in a traditional CS-based approach.

Figure 2:
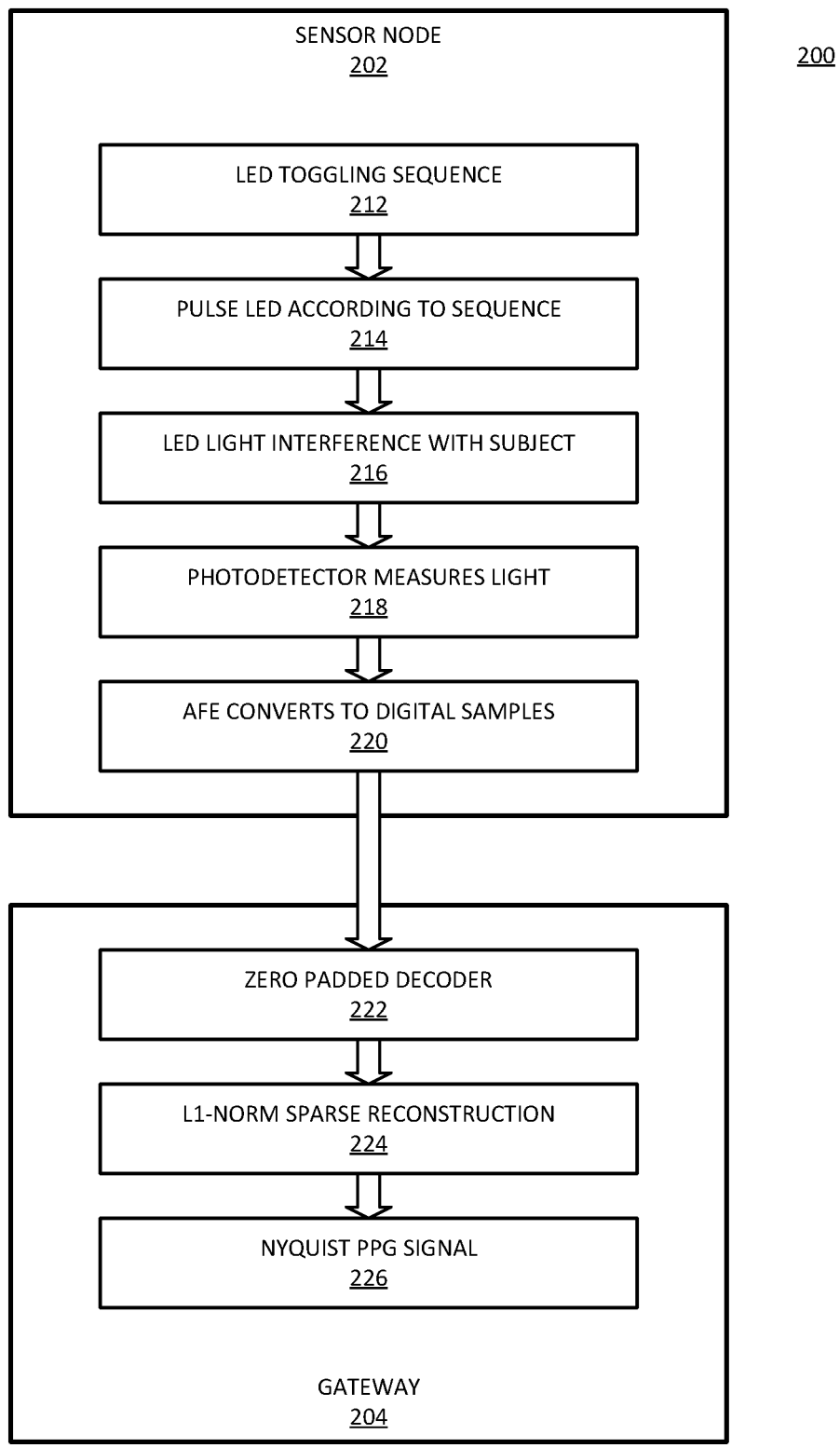
FIG. 2 is a block diagram of an embodiment of a system for PPG signal reconstruction from a sparse measurement matrix.

FIG. 2 is a block diagram of an embodiment of a system for PPG signal reconstruction from a sparse measurement matrix. System 200 provides one example of a pulse oximeter system in accordance with an embodiment of system 100 of FIG. 1. Whereas system 100 provided one representation of simplified system hardware, system 200 illustrates a simplified representation of the data processing pipeline of a PPG measurement system in accordance with any embodiment described herein. System 200 specifically illustrates sensor node 202 and gateway 204. Sensor node 202 refers to hardware elements that generate measurement data through interaction with a subject. Gateway 204 refers to a processing unit that receives the measurement data and performs PPG signal recovery from the measurement data. In one embodiment, sensor node 202 and gateway 204 are part of the same physical device. In one embodiment, sensor node 202 and gateway 204 are part of two separate physical devices, and are communicatively coupled.

Sensor node 202 can be considered the "acquisition" side of the data processing, referring to the fact that it generates the measurement data used to recover the PPG signal. Gateway 204 can be considered the "processing" side or the reconstruction side of the data processing. In one embodiment, system 200 represents an asymmetric system architecture. In an asymmetric architecture, sensor node 202 is computationally constrained, by having low computational capability to save power. Gateway 204 is not computationally constrained, and can perform the computations necessary for signal reconstruction.

Figures 3A, 3B:
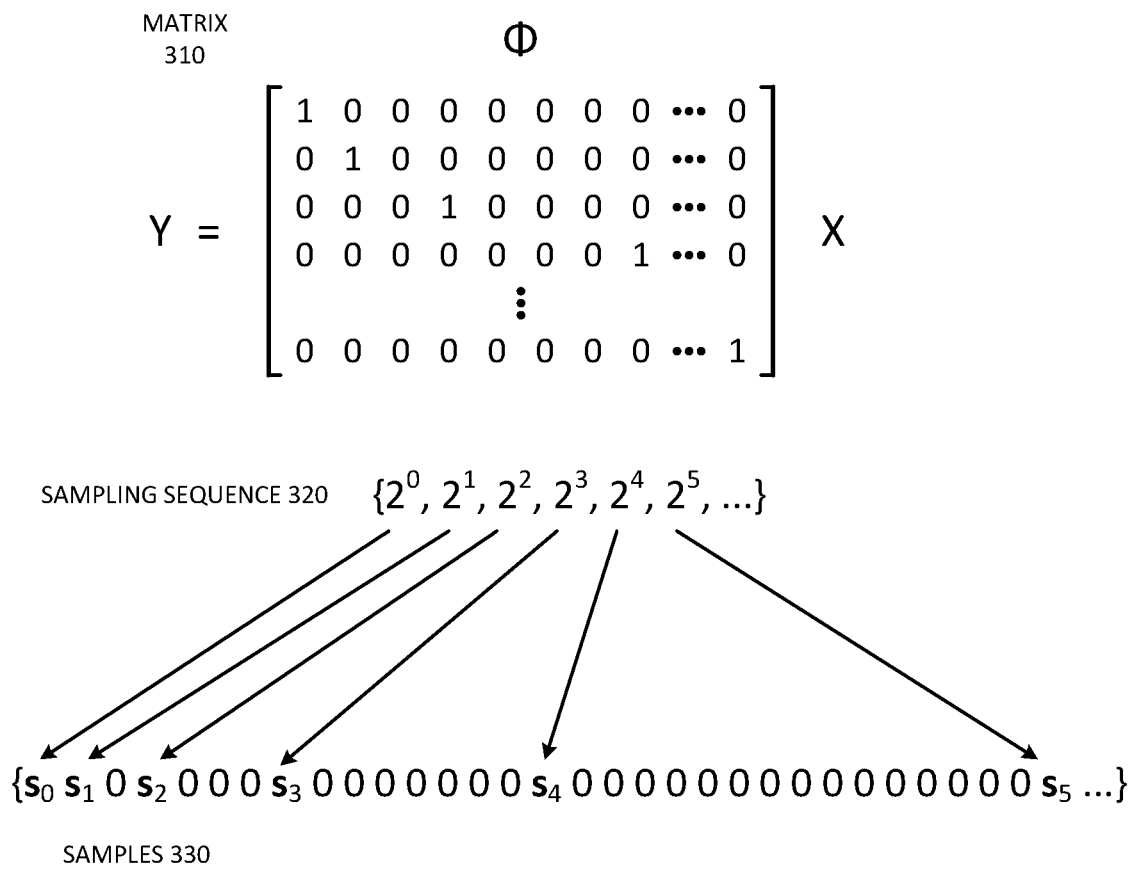
FIG. 3A is a representation of an embodiment of a compressive sensing reconstruction matrix, with a mapping of the sampling sequence.
FIG. 3B is a representation of an embodiment of a zero-padded compressive sensing reconstruction matrix.

In one embodiment, sensor node 202 includes performs an LED toggling sequence, 212, to produce a non-uniform toggling of the acquisition LED(s). The LED toggling sequence can be or include logic or an encoder to capture most of the principal frequencies in the bandlimited PPG signal. In one embodiment, the LED toggling sequence causes an LED to emit light pulses in accordance with the toggling sequence, which generates a series of measurement data in accordance with the timing of the toggling sequence. Thus, in a compressive sensing analysis, the LED toggling sequence can be considered encoder logic or a sparse measurement matrix. FIG. 3A provides one example of a toggling sequence matrix that can be implemented as the LED toggling sequence.

Sensor node 202 pulses the LED according to the sequence, 214. The light pulses interfere with the subject, 216, and a photodetector measures the light, 218. Based on the timing of the LED pulses (data in the time domain), the photodetector correspondingly generates measurement data in the time domain. The measurements represent data to fill the sparse measurement matrix. In one embodiment, an AFE of sensor node 202 converts the measurements into digital data samples, 220, for sending to gateway 204.

In one embodiment of system 200, all data processing is handled by gateway 204. Thus, sensor node 202 may convert the measurement data into digital format, but does not perform any pre-processing on the data. Thus, sensor node 202 can send raw data to gateway 202. The raw data is not processed for purposes of filtering, correcting for noise, or other processing operations. With a small number of raw data samples, the transmission from sensor node 202 to gateway 204 is lower power and simplified. Additionally, the buffering and pipelining of data at gateway 204 can be simplified. In one embodiment, sensor node 202 sends every measurement as it is obtained and converted to digital representation. In one embodiment, sensor node 202 buffers data and sends it to gateway 204 in a batch.

At gateway 204, in one embodiment, the gateway performs L1-norm-based reconstruction. In one embodiment, gateway 204 zero-pads the data measurements received from sensor node 202. Such an operation can be considered as gateway 202 applying a zero padded decoder, 222. Gateway 202 can thus include padding logic to enhance bin resolution for an L1-norm recovery algorithm. The zero padding can enable processing or computation logic (e.g., a processor or processing unit) on gateway 204 to more accurately localize frequency coefficients during reconstruction. In one embodiment, the processor performs an L1-norm sparse matrix reconstruction, 224, to recover the PPG signal. Through reconstruction, the processor generates a Nyquist PPG signal, 226, referring to a PPG signal representation that has the data of or nearly identical data to a PPG signal generated based on Nyquist sampling.

The reconstruction of the PPG signal or recovery of the signal refer to computing frequency coefficients. In one embodiment the PPG signal reconstruction includes performance of computations based on a Fourier transform, such as an FFT (fast Fourier transform) for the measurement matrix. The reconstruction of the PPG signal is understood to include computations based on the sparse basis representation of the signal as indicated by the sparsely spaced signal measurements. The signal measurements should include enough frequency information to recover the frequency coefficients to generate a representation of the signal. The zero padding can be padding of the sparse basis representation measurements.

To compute the correct coefficients for the frequency components to obtain an accurate representation of the signal, the processor needs the placement of the measurement data localized to the right bin, or the right column within the matrix. It will be understood that a "Nyquist" representation of a PPG signal includes a 32 Hz signal, which typically includes 32 frequency bands, or 32 bins with 1 Hz spacing. Computation on non-zero-padded measurement data provides adequate placement, but does not have very good granularity. The zero padding causes the processor to increase the number of bins, which in turn increases the bin spacing for the same signal, or produces a wider range of computation for recovering the signal information. The increased number of bins increases the computational cost of the L1-norm computations, but provides a more accurate end result.

Thus, system 200 can recover the original PPG signal with high reconstruction accuracy from sparse measurements in a highly power efficient manner. The LED toggling schedule is easily embeddable on a resource-constrained sensor node 202 and is also highly power-efficient.

FIG. 3A is a representation of an embodiment of a compressive sensing reconstruction matrix, with a mapping of the sampling sequence. In one embodiment, matrix 310 (matrix $\Phi$) can be referred to as encoder logic represented as a sparse measurement matrix. X represents the notional continuous time-domain PPG signal. The columns of matrix 310 represent the time instant of sampling (and correspond to exciting or pulsing the LED). The number of rows in matrix 310 represent number of samples taken in accordance with the compressive sensing logic. The number of samples taken is significantly reduced relative to other approaches. The rows in measurement matrix 310 are populated with only a single '1', to indicate that each measured raw PPG sample is directly used as an encoded value. Therefore, matrix 310 can be considered the sparsest encoder that can be used to recover the PPG signal. In one embodiment, to capture the most information possible, matrix 310 allocates a single '1' in each row to specific columns of the measurement matrix, where the column indices form a geometric progression.

As represented in matrix 310, the temporal spacing of individual measurements corresponds to a binary-sequence (powers of 2). The spacing is more explicitly pointed out by sampling sequence 320. Sampling sequence 320 represents a fixed schedule for generating measurements. In one embodiment, the fixed schedule is adjustable in accordance with the subject or the person whose measurements will be taken and the purpose for the measurements. The schedule or sequence 320 can be adjustable by adjusting how many measurements or how many elements will be generated, depending on what measurements are made and what the subject of the measurement is. When the schedule can be adjusted, a system can be preconfigured with the appropriate schedule based on the subject and the implementation of the system.

In one embodiment, sampling sequence 320 is $2^i$, where i is the sample number. Samples 330 illustrate the samples acquired in accordance with sampling sequence 320, with samples $s_i$ separated by a number of zeros equal to $2^{(i-1)}-1$ from the previous sample. Thus, in one embodiment for a 1-second support window, the order of samples acquired is 1, 2, 4, 8, 16, . . . . As illustrated, sample $s_2$ is separated from sample $s_1$ by 1 zero (($2^{(2-1)})-1$), sample $s_3$ is separated from sample $s_2$ by 3 zeros (($2^{(3-1)})-1$), and so forth. In one embodiment, sampling schedule 320 is fixed across all sampling windows (e.g., every 10-second sampling window, or other sampling window).

In one embodiment, Y represents the sub-sampled LED measurements. In one embodiment, a sensor node AFE transmits Y directly to a gateway device via Bluetooth LE, and the gateway reconstructs the entire PPG signal. A conventional L1-norm recovery algorithm can be represented as: min $\{\|x\|_1: \Phi\psi^{-1}x=y\}$, where $\Phi$ represents the sparse measurement matrix or signal decoder matrix (e.g., matrix 310), $\psi^{-1}$ represents the sparse basis representation matrix (e.g., the inverse of the discrete Fourier transform (DFT) representation matrix), y represents the encoded signal, and x represents a corresponding recovered signal in the sparse basis.

FIG. 3B is a representation of an embodiment of a zero-padded compressive sensing reconstruction matrix. In one embodiment, the gateway cannot recover the entire PPG signal with required accuracy from an extremely sparse matrix such as matrix 310 by use of a conventional L1-norm recovery algorithm. Matrix 340 represents an augmented or zero padded decoding matrix. Matrix 340 can be generated from matrix 310 by padding logic that will improve the accuracy with which the undersampled signal can be reconstructed in the discrete Fourier basis. As illustrated, matrix 340 includes the sensor node measurement matrix portion 342, and includes augmented zero padding portion 344. While eight zeros are shown, it will be understood that zero padding 344 can include any number of zeros.

Matrix 340 represents an augmented sparse measurement matrix that provides increased bin resolution during recovery, and can significantly reduce reconstruction error. Matrix 340 could be represented as $\Phi'$, referring to the mathematical representation for matrix 310 above. In one embodiment, the processor on the gateway side implements the conventional recovery algorithm as set out above, but with $\Phi'$ instead of $\Phi$. Experimentation has shown that padding size ranges from 100-400 padded elements for a 32 Hz PPG (with window support=105) offer best performance. The extent of padding required increases with the sampling frequency for a similar performance improvement.

Both the encoder matrix 310 of FIG. 3A and zero padded encoder matrix 340 of FIG. 3B are highly incoherent with the DFT (discrete Fourier transform) representation matrix $\psi$). Coherency refers to a measure of how much redundancy in information exists in the sample points or measurements. Low coherency indicates that more of the measurement signal information is actual data, rather than redundant information. The below table indicates the matrix dimensions, and indicates a coherency value of "1" for the matrices.

| Compression ratio | Encoding matrix dimensions (m × n) | Decoding matrix dimensions after padding | Acceptable Coherence Range $(1, \sqrt{n})$ | Coherence for Encoding Matrix | Coherence for Decoding Matrix |
|---|---|---|---|---|---|
| CR = 2 to CR = 10 | 160 × 320 to 32 × 320 | 160 × 520 to 32 × 520 | (1, 22.8) | 1 | 1 |

It will be understood that the padding refers to inserting zero values into the sparse measurement matrix. Inserting the zeros increases the number of bins in the decoding process. The number of bins refers to a bin width or integration range, which refers to a number of elements to be used in computation. Increasing the bin spacing provides finer grain computation for recovering signal information outside the main lobe of the bin. Increasing the bin spacing results in a higher computational requirement, but provides more accurate signal recovery.

Figure 4A:
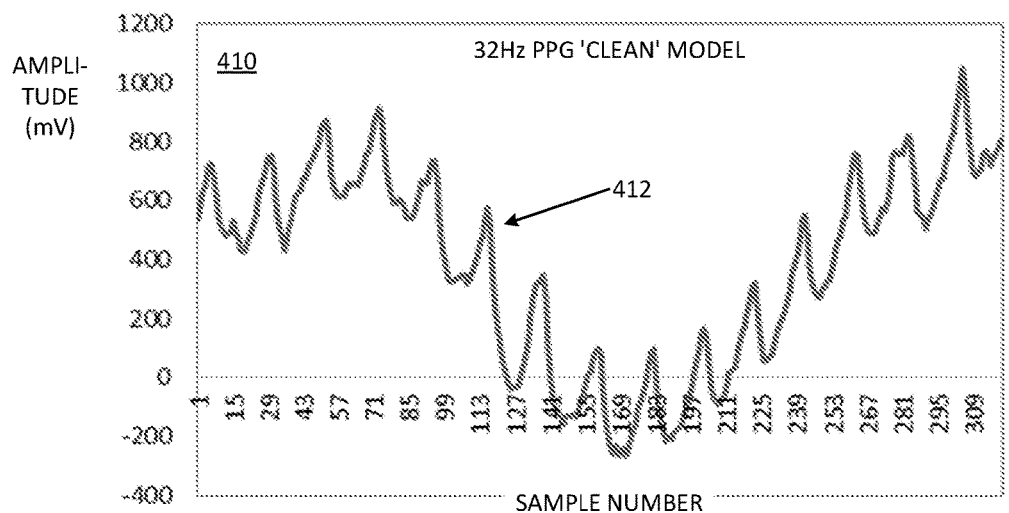
FIGS. 4A-4C are diagrammatic representations of an embodiment of a recovered PPG signal in accordance with compressive sensing reconstruction in a controlled environment.
Figure 4B:
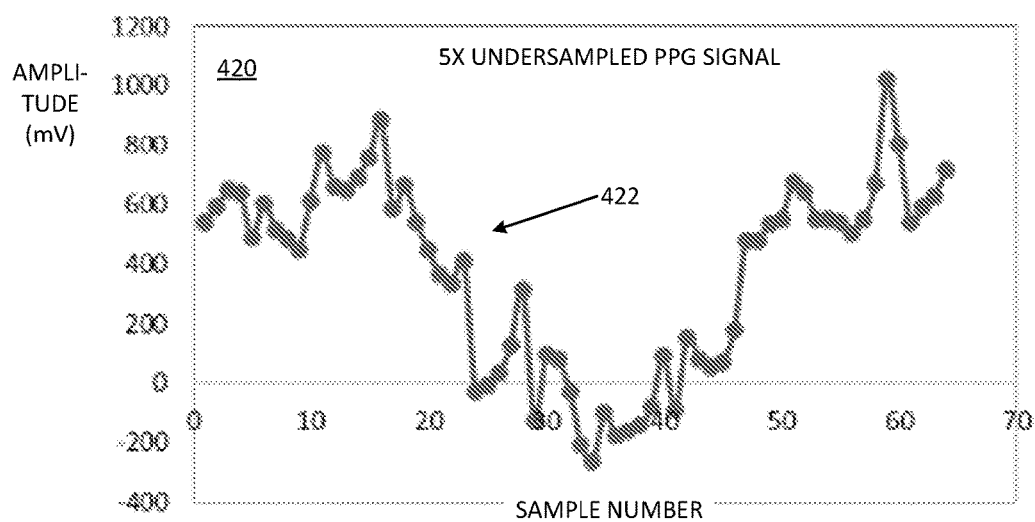
Figure 4C:
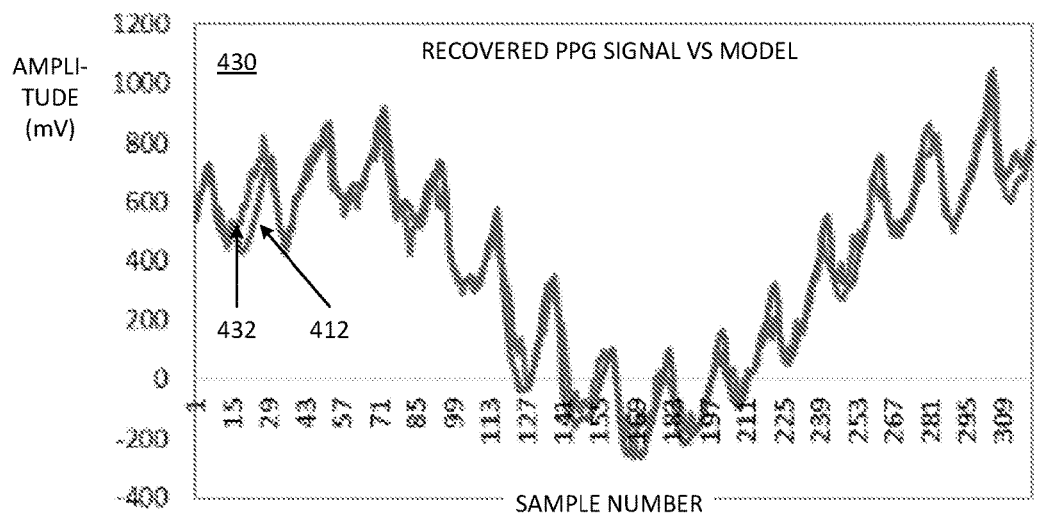

FIGS. 4A-4C are diagrammatic representations of an embodiment of a recovered PPG signal in accordance with compressive sensing reconstruction in a controlled environment. In the controlled environment, the PPG signal is recovered in a "clean" environment, or an environment controlled for noise. Diagram 410 of FIG. 4A includes signal 412, which represent an input 32 Hz Nyquist PPG signal, which is the shape of a PPG signal as sampled at 32 Hz. Signal 412 is generated from the number of samples along the x-axis measured at amplitude points along the y-axis. The measurements of diagram 420 and the reconstruction of diagram 430 were performed by a prototype of the system in accordance with an embodiment of what is described herein. As illustrated, the reconstruction processor applied zero padding to the undersampled data.

Diagram 420 of FIG. 4B illustrates an undersampling representation of the signal. Undersampled curve 422 is a graphing of sample points connected by lines. Diagram 420 also illustrates the number of samples on the x-axis plotted against amplitude on the y-axis. It will be observed that diagram 420 includes 5 times fewer samples than diagram 410, illustrating the fact that it is 5× undersampled. It will also be observed from the sample points on curve 422 that the PPG signal has been non-uniformly under-sampled by toggling one or more LEDs via a sampling schedule in accordance with a CS-based measurement matrix, as described above.

Diagram 430 of FIG. 4C illustrates signal 432, which represents a reconstructed signal obtained by processing the measurement data of curve 422. More specifically, signal 432 is plotted overlaying the plot of signal 412 of diagram 410. There are a few areas of separation between signals 412 and 432 (the white space between the two signal lines), but it will be observed how closely signal 432 tracks to signal 412. Whereas signal 412 was obtained by sampling at 32 Hz, signal 432 was obtained by 5X undersampling, with a nearly identical reconstructed signal representation as signal 412, showing the recovery accuracy of the system as described herein.

Figure 5A:
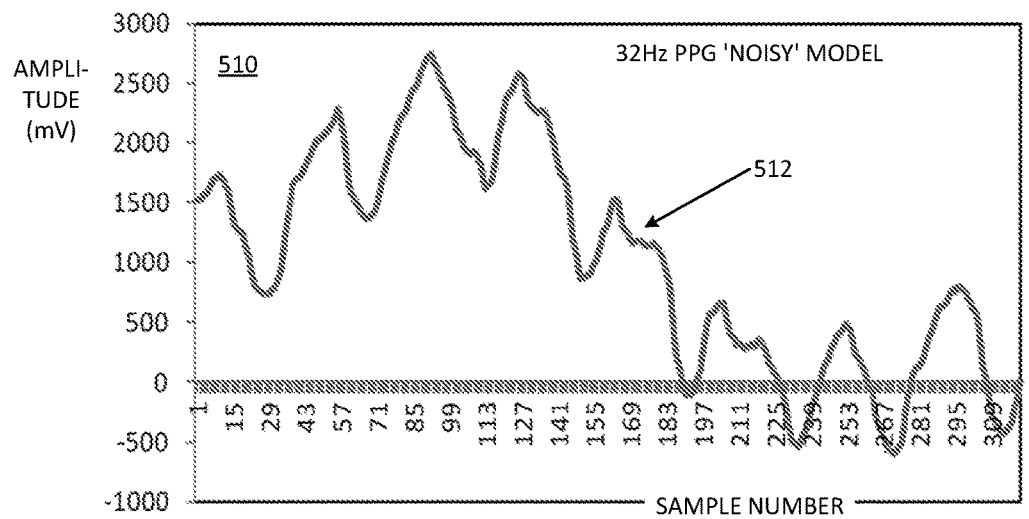
FIGS. 5A-5C are diagrammatic representations of an embodiment of a recovered PPG signal in accordance with compressive sensing reconstruction in a noisy environment.
Figure 5B:
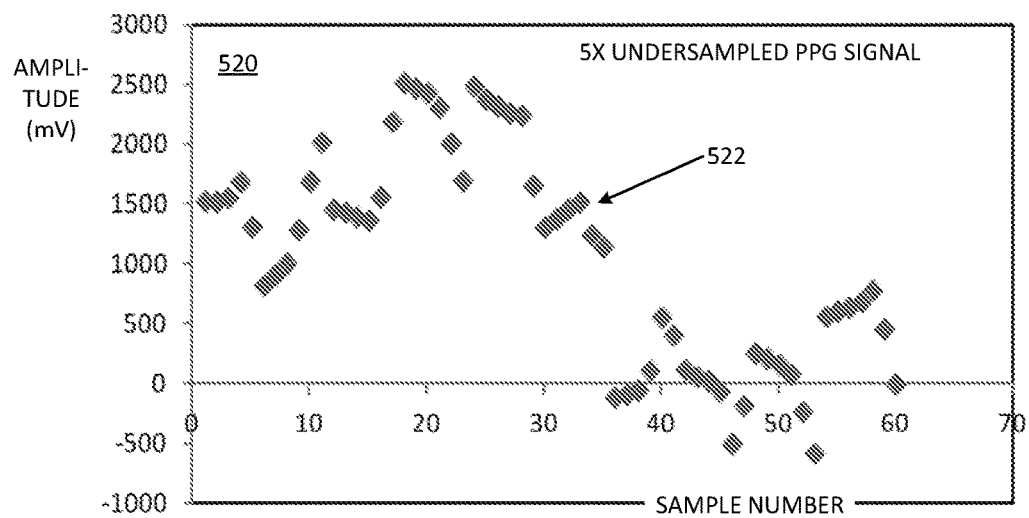
Figure 5C:
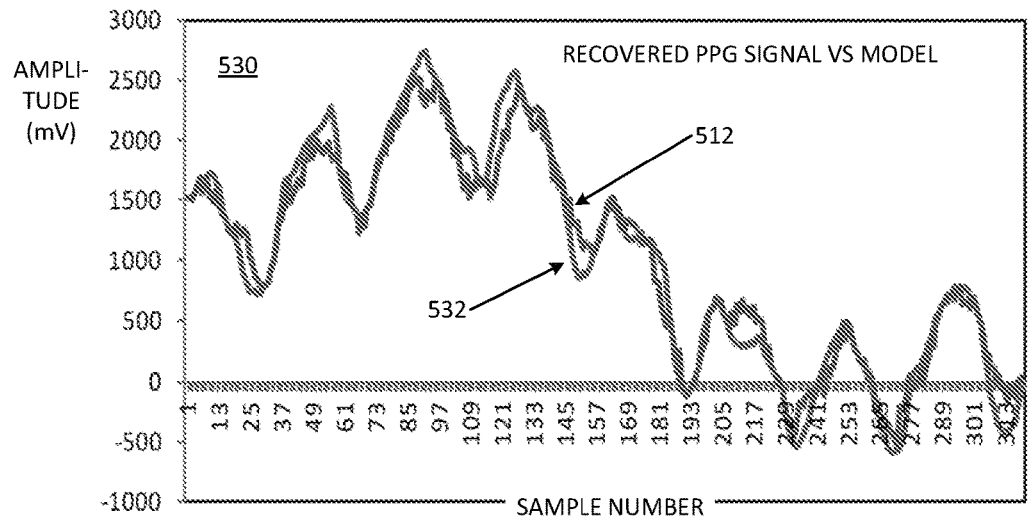

FIGS. 5A-5C are diagrammatic representations of an embodiment of a recovered PPG signal in accordance with compressive sensing reconstruction in a noisy environment. It will be understood that the signal processing pipeline described should reproduce the morphology of the input signal even if operated in noisy conditions. In the noisy environment, the PPG signal is recovered from a noisy signal. Diagram 510 of FIG. 5A includes signal 512, which represent an input 32 Hz Nyquist PPG signal, which is the shape of a PPG signal as sampled at 32 Hz. Signal 512 is generated from the number of samples along the x-axis measured at amplitude points along the y-axis. The measurements of diagram 520 and the reconstruction of diagram 530 were performed by a prototype of the system in accordance with an embodiment of what is described herein. As illustrated, the reconstruction processor applied zero padding to the undersampled data.

Diagram 520 of FIG. 5B illustrates an undersampling representation of the signal. Undersampled plot points 522 is a plotting of measurement sample points. Diagram 520 also illustrates the number of samples on the x-axis plotted against amplitude on the y-axis. It will be observed that diagram 520 includes 5 times fewer samples than diagram 510, illustrating the fact that it is 5× undersampled. It will also be observed from plot points 522 that the PPG signal has been non-uniformly under-sampled by toggling one or more LEDs via a sampling schedule in accordance with a CS-based measurement matrix, as described above.

Diagram 530 of FIG. 5C illustrates signal 532, which represents a reconstructed signal obtained by processing the measurement data of plot points 522. More specifically, signal 532 is plotted overlaying the plot of signal 512 of diagram 510. As with the "clean" PPG signal referred to above with respect to FIG. 4C, in diagram 530 there are areas of separation between signals 512 and 532 (the white space between the two signal lines), but it will be observed how closely signal 532 tracks to signal 512. Whereas signal 512 was obtained by sampling at 32 Hz, signal 532 was obtained by 5X undersampling, with a nearly identical reconstructed signal representation as signal 512, showing the recovery accuracy of the system as described herein, even when sampling a noisy signal.

FIGS. 6A-6D are diagrammatic representations of power savings obtained by a PPG measurement system in accordance with an embodiment of compressive sensing PPG signal reconstruction. Diagram 610 of FIG. 6A illustrates a comparison of the LED undersampling ratio (x-axis) versus the number of errors (y-axis). More specifically, curve 612 illustrates the number of errors versus undersampling ratio for the compressive sensing PPG signal reconstruction described herein. Curve 614 illustrates the number of errors versus undersampling ratio for a prior compressive sensing recovery technique that used random sampling instead of fixed pattern sampling as described. The specific curve in diagram 610 was generated by a system that also used a binary sampling sequence and applied zero padding to the signal reconstruction. It will be observed that despite obtaining fewer samples, the fixed pattern sampling described herein provided improved error performance.

Table 620 of FIG. 6B illustrates tabular results to support graphical diagram 610. Two different signal requirements were used as test conditions. In the first, the systems were required to reconstruct a 32 Hz PPG signal, and in the second were required to reconstruct a 100 Hz PPG signal.

For the 32 Hz PPG signal, one embodiment of a system in accordance with what is described herein was able to reconstruct the signal from 6 LED samples per second for a 2% error in heartrate data. To obtain a signal that provided only 2% error in heartrate data for the traditional CS technique, the other system required 12 samples per second, or twice as much sampling.

The 100 Hz PPG signal reconstruction illustrates that the technique scales to higher frequencies. As illustrated, for a signal reconstruction with 98% heartrate extraction accuracy, the traditional system required 22 samples per second, while an embodiment of a system in accordance with what is described herein required only 11 samples per second. In general, compared to the traditional system, the system described herein can reduce LED toggling rates by as much as 2×-4× under constraints of both reconstruction error (PRD % such as illustrated in diagram 610 of FIG. 6A) and 98% heartrate extraction accuracy (HR % such as illustrated in table 620 of FIG. 6B).

Diagram 630 of FIG. 6C illustrates power savings as compared between an embodiment of a system in accordance with what is described herein, and a traditional 32 Hz sampling system. The power characterization of diagram 630 illustrates actual results of test systems. Bar graph 632 illustrates total power usage, and power usage broken down by PPG system component, for an embodiment of a system in accordance with what is described herein. Bar graph 634 illustrates total power usage, and power usage broken down by PPG system component, for a traditional continuous sampling system.

BTLE (Bluetooth LE) represents the power usage for a radio component to send from a sensor node to a computing gateway, which for the illustrations provided in diagram 630 included a wristband sensor implementation to a laptop computer gateway. Compute power represents the power for computational components (e.g., a microcontroller) of the sensor system. AFE power represents the power for driving the LED and converting detected signals into digital representation. LED power represents the amount of power consumed by the LED.

Table 650 of FIG. 6D illustrates tabular information corresponding to diagram 630. As illustrated, LED power reduction for a system described herein was 80% over the traditional system. Total sensor node system power saving of 68% compared to a standard 32 Hz PPG acquisition system. Thus, it will be understood that a PPG acquisition system can have significantly reduced data acquisition power without loss of heartrate estimation accuracy.

Figure 7A:
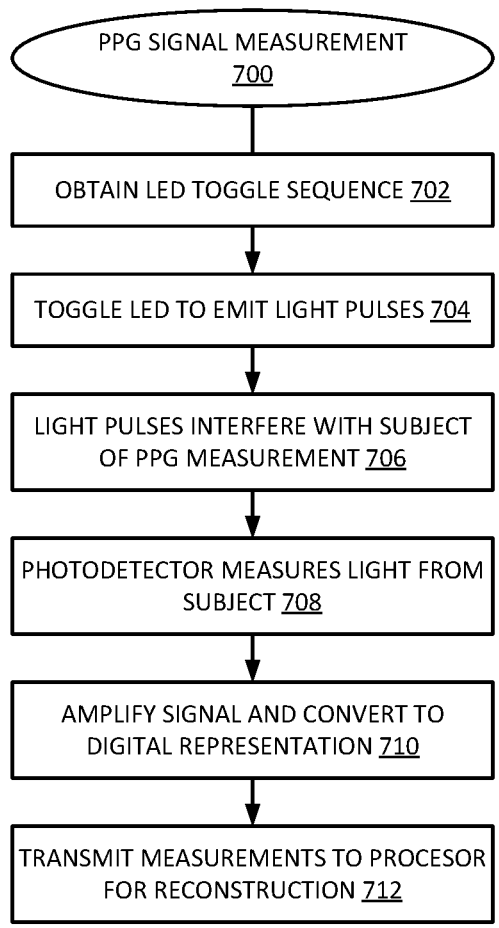
FIG. 7A is a flow diagram of an embodiment of a process for generating a sparse measurement matrix for compressive sensing PPG signal reconstruction.

FIG. 7A is a flow diagram of an embodiment of a process for generating a sparse measurement matrix for compressive sensing PPG signal reconstruction. Process 700 illustrates operations for PPG signal measurement by a sensor node in accordance with an embodiment of a sensor system described herein. In one embodiment, the sensor system obtains an LED toggle sequence, 702. In one embodiment, the sensor node is preprogrammed with the toggle sequence. For example, the sensor node may include one or more computing components that trigger an LED driver to operate in accordance with a fixed LED toggle sequence.

The driver drives the LED to emit light pulses in accordance with the fixed pattern, 704. The light pulses from the LED interfere with a subject for PPG measurement, 706. In one embodiment, light pulses penetrate the subject's skin. In one embodiment, light pulses reflect off the surface of the subject's skin. A photodetector measures the light from the subject, 708. In one embodiment, an AFE receives signals from the photodetector and amplifies the signal and converts them to a digital representation, 710. It will be understood that the sensor node acquires PPG measurements over a measurement window, which generates a series of measurement data corresponding to the fixed toggling schedule. The series of measurement data can be non-uniform in the time-domain, with different timing delays between samples. The series of samples correspond to a sparse sample matrix to be used in reconstruction.

In one embodiment, the AFE transmits signals one at a time to a processing unit. In one embodiment, the AFE buffers multiple measurements and transmits them in a batch. In either case the AFE transmits the measurements to a processor component for compressive sensing reconstruction of the PPG signal from the measurement matrix data, 712. In one embodiment, the AFE transmits raw measurement data to the processor. In one embodiment, the AFE generates the measurement matrix prior to sending the data to the processor. In one embodiment, the processor generates the measurement matrix from measurement data sent by the sensor node. In one embodiment, the sensor node and the processor node are in separate devices.

Figure 7B:
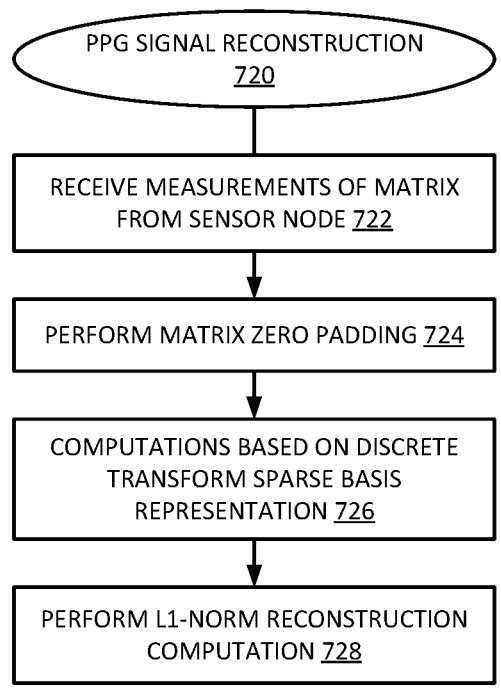
FIG. 7B is a flow diagram of an embodiment of a process for applying compressive sensing to a sparse measurement matrix for PPG signal reconstruction.

FIG. 7B is a flow diagram of an embodiment of a process for applying compressive sensing to a sparse measurement matrix for PPG signal reconstruction. Process 720 represents operations for PPG signal reconstruction that can be performed by a processor node of a PPG system. The processor node receives measurement data from a sensor node, 722. In one embodiment, the processor node generates a measurement matrix from the received data. In one embodiment, the processor node performs zero padding on the measurement matrix, 724. The zero padding can be in accordance with what is described above, which can improve the quality of the recovered PPG signal.

In one embodiment, the processor node performs computations based on a discrete transform sparse basis representation, 726. For example, the transform can be or include a discrete Fourier transform, a discrete cosine transform, or other transform. The processor node performs computations based on the transform for reconstruction and signal estimation. The transform can be part of an L1-norm reconstruction. The processor performs L1-norm reconstruction computations to generate frequency coefficients to specify the PPG signal, 728.

Figure 8:
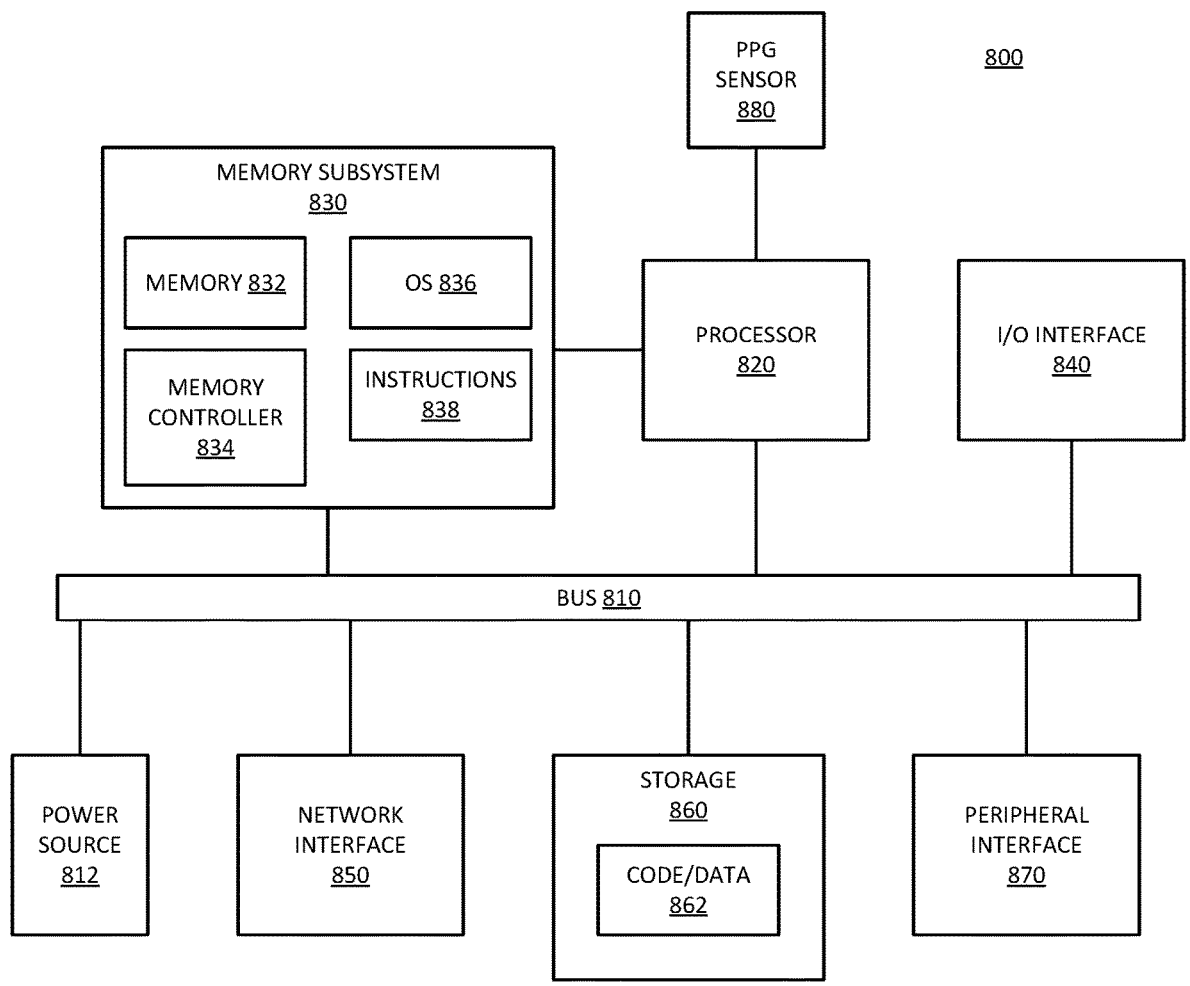
FIG. 8 is a block diagram of an embodiment of a computing system in which a compressive sensing PPG signal reconstruction system can be implemented.

FIG. 8 is a block diagram of an embodiment of a computing system in which a compressive sensing PPG signal reconstruction system can be implemented. System 800 represents a computing device in accordance with any embodiment described herein, which can provide a processing unit or a gateway in accordance with any embodiment described herein. System 800 can be a laptop computer, a desktop computer, a server, a gaming or entertainment control system, a scanner, copier, printer, routing or switching device, or other electronic device. System 800 includes processor 820, which provides processing, operation management, and execution of instructions for system 800. Processor 820 can include any type of microprocessor, central processing unit (CPU), processing core, or other processing hardware to provide processing for system 800. Processor 820 controls the overall operation of system 800, and can be or include, one or more programmable general-purpose or special-purpose microprocessors, digital signal processors (DSPs), programmable controllers, application specific integrated circuits (ASICs), programmable logic devices (PLDs), or the like, or a combination of such devices. Processor 820 can execute data stored in memory 832 and/or write or edit data stored in memory 832.

Memory subsystem 830 represents the main memory of system 800, and provides temporary storage for code to be executed by processor 820, or data values to be used in executing a routine. Memory subsystem 830 can include one or more memory devices such as read-only memory (ROM), flash memory, one or more varieties of random access memory (RAM), or other memory devices, or a combination of such devices. Memory subsystem 830 stores and hosts, among other things, operating system (OS) 836 to provide a software platform for execution of instructions in system 800. Additionally, other instructions 838 are stored and executed from memory subsystem 830 to provide the logic and the processing of system 800. OS 836 and instructions 838 are executed by processor 820. Memory subsystem 830 includes memory device 832 where it stores data, instructions, programs, or other items. In one embodiment, memory subsystem includes memory controller 834, which is a memory controller to generate and issue commands to memory device 832. It will be understood that memory controller 834 could be a physical part of processor 820.

Processor 820 and memory subsystem 830 are coupled to bus/bus system 810. Bus 810 is an abstraction that represents any one or more separate physical buses, communication lines/interfaces, and/or point-to-point connections, connected by appropriate bridges, adapters, and/or controllers. Therefore, bus 810 can include, for example, one or more of a system bus, a Peripheral Component Interconnect (PCI) bus, a HyperTransport or industry standard architecture (ISA) bus, a small computer system interface (SCSI) bus, a universal serial bus (USB), or an Institute of Electrical and Electronics Engineers (IEEE) standard 1394 bus (commonly referred to as "Firewire"). The buses of bus 810 can also correspond to interfaces in network interface 850.

Power source 812 couples to bus 810 to provide power to the components of system 800. In one embodiment, power source 812 includes an AC to DC (alternating current to direct current) adapter to plug into a wall outlet. Such AC power can be renewable energy (e.g., solar power). In one embodiment, power source 812 includes only DC power, which can be provided by a DC power source, such as an external AC to DC converter. In one embodiment, power source 812 includes wireless charging hardware to charge via proximity to a charging field. In one embodiment, power source 812 can include an internal battery or fuel cell source.

System 800 also includes one or more input/output (I/O) interface(s) 840, network interface 850, one or more internal mass storage device(s) 860, and peripheral interface 870 coupled to bus 810. I/O interface 840 can include one or more interface components through which a user interacts with system 800 (e.g., video, audio, and/or alphanumeric interfacing). In one embodiment, I/O interface 840 generates a display based on data stored in memory and/or operations executed by processor 820. Network interface 850 provides system 800 the ability to communicate with remote devices (e.g., servers, other computing devices) over one or more networks. Network interface 850 can include an Ethernet adapter, wireless interconnection components, USB (universal serial bus), or other wired or wireless standards-based or proprietary interfaces. Network interface 850 can exchange data with a remote device, which can include sending data stored in memory and/or receive data to be stored in memory.

Storage 860 can be or include any conventional medium for storing large amounts of data in a nonvolatile manner, such as one or more magnetic, solid state, or optical based disks, or a combination. Storage 860 holds code or instructions and data 862 in a persistent state (i.e., the value is retained despite interruption of power to system 800). Storage 860 can be generically considered to be a "memory," although memory 830 is the executing or operating memory to provide instructions to processor 820. Whereas storage 860 is nonvolatile, memory 830 can include volatile memory (i.e., the value or state of the data is indeterminate if power is interrupted to system 800).

Peripheral interface 870 can include any hardware interface not specifically mentioned above. Peripherals refer generally to devices that connect dependently to system 800. A dependent connection is one where system 800 provides the software and/or hardware platform on which operation executes, and with which a user interacts.

In one embodiment, system 800 includes an interface to PPG sensor 880. In one embodiment, PPG sensor 880 couples directly to processor 820. In one embodiment, PPG sensor 880 couples to processor 820 via peripheral interface 870 or other connection of system 800. PPG sensor 880 generates sparse measurement matrix data samples in accordance with any embodiment described herein. PPG sensor 880 measures data in accordance with a fixed pattern. The pattern can be non-uniform. The pattern can be a binary progression sequence. The sensor transmits the measurement data to processor 820 for PPG signal recovery based on compressive sensing reconstruction computations. System 800 can operate as a gateway device to perform the computations based on the sparse matrix. In one embodiment, processor 820 performs zero padding of the measurement data from PPG sensor 880.

Figure 9:
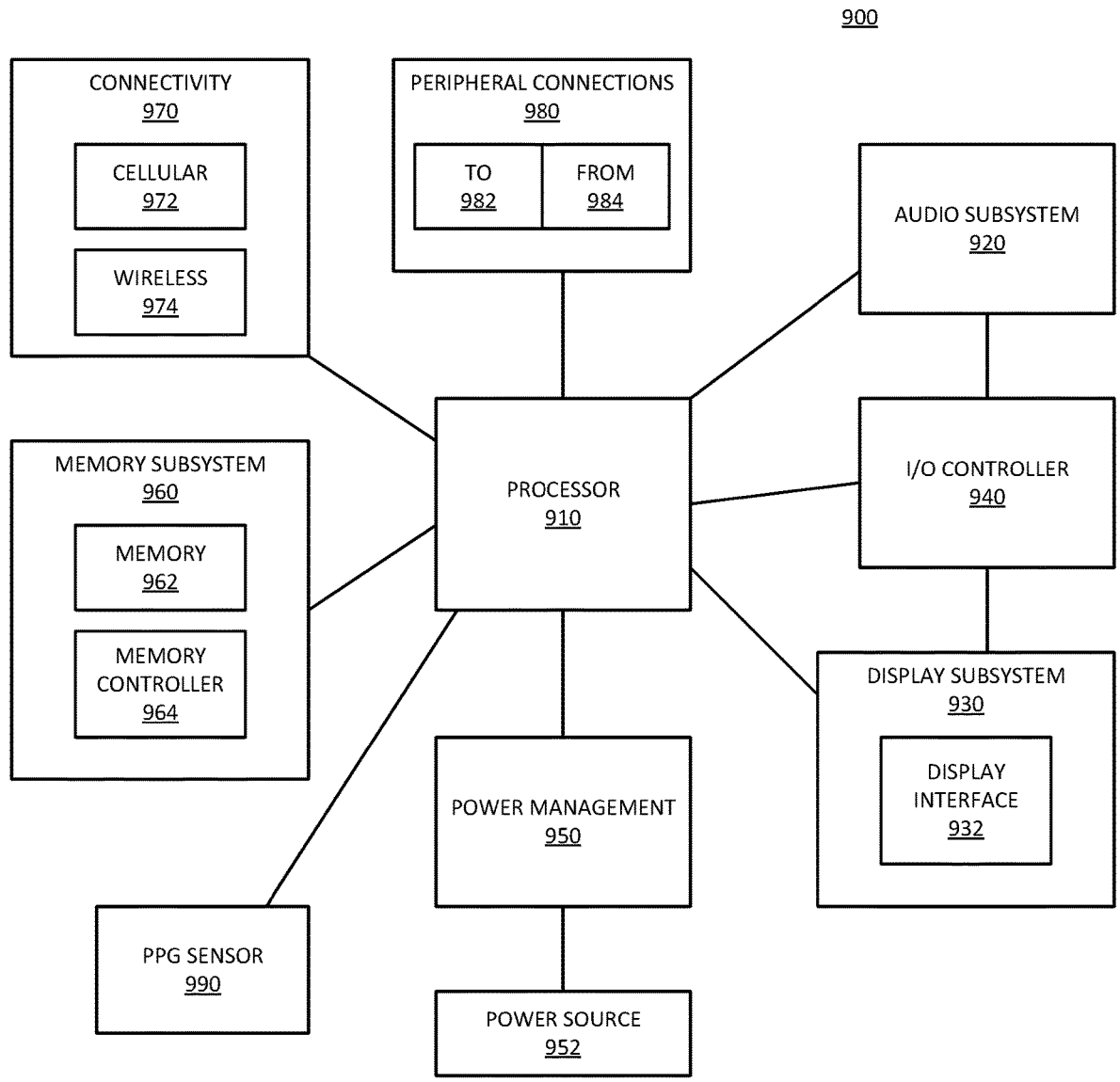
FIG. 9 is a block diagram of an embodiment of a mobile device in which a compressive sensing PPG signal reconstruction system be implemented.

FIG. 9 is a block diagram of an embodiment of a mobile device in which a compressive sensing PPG signal reconstruction system be implemented. Device 900 represents a mobile computing device, such as a computing tablet, a mobile phone or smartphone, a wireless-enabled e-reader, wearable computing device, or other mobile device. It will be understood that certain of the components are shown generally, and not all components of such a device are shown in device 900.

Device 900 includes processor 910, which performs the primary processing operations of device 900. Processor 910 can include one or more physical devices, such as microprocessors, application processors, microcontrollers, programmable logic devices, or other processing means. The processing operations performed by processor 910 include the execution of an operating platform or operating system on which applications and/or device functions are executed. The processing operations include operations related to I/O (input/output) with a human user or with other devices, operations related to power management, and/or operations related to connecting device 900 to another device. The processing operations can also include operations related to audio I/O and/or display I/O. Processor 910 can execute data stored in memory and/or write or edit data stored in memory.

In one embodiment, device 900 includes audio subsystem 920, which represents hardware (e.g., audio hardware and audio circuits) and software (e.g., drivers, codecs) components associated with providing audio functions to the computing device. Audio functions can include speaker and/or headphone output, as well as microphone input. Devices for such functions can be integrated into device 900, or connected to device 900. In one embodiment, a user interacts with device 900 by providing audio commands that are received and processed by processor 910.

Display subsystem 930 represents hardware (e.g., display devices) and software (e.g., drivers) components that provide a visual and/or tactile display for a user to interact with the computing device. Display subsystem 930 includes display interface 932, which includes the particular screen or hardware device used to provide a display to a user. In one embodiment, display interface 932 includes logic separate from processor 910 to perform at least some processing related to the display. In one embodiment, display subsystem 930 includes a touchscreen device that provides both output and input to a user. In one embodiment, display subsystem 930 includes a high definition (HD) display that provides an output to a user. High definition can refer to a display having a pixel density of approximately 90 PPI (pixels per inch) or greater, and can include formats such as full HD (e.g., 980p), retina displays, 4K (ultra high definition or UHD), or others. In one embodiment, display subsystem 930 generates display information based on data stored in memory and/or operations executed by processor 910.

I/O controller 940 represents hardware devices and software components related to interaction with a user. I/O controller 940 can operate to manage hardware that is part of audio subsystem 920 and/or display subsystem 930. Additionally, I/O controller 940 illustrates a connection point for additional devices that connect to device 900 through which a user might interact with the system. For example, devices that can be attached to device 900 might include microphone devices, speaker or stereo systems, video systems or other display device, keyboard or keypad devices, or other I/O devices for use with specific applications such as card readers or other devices.

As mentioned above, I/O controller 940 can interact with audio subsystem 920 and/or display subsystem 930. For example, input through a microphone or other audio device can provide input or commands for one or more applications or functions of device 900. Additionally, audio output can be provided instead of or in addition to display output. In another example, if display subsystem includes a touchscreen, the display device also acts as an input device, which can be at least partially managed by I/O controller 940. There can also be additional buttons or switches on device 900 to provide I/O functions managed by I/O controller 940.

In one embodiment, I/O controller 940 manages devices such as accelerometers, cameras, light sensors or other environmental sensors, gyroscopes, global positioning system (GPS), or other hardware that can be included in device 900. The input can be part of direct user interaction, as well as providing environmental input to the system to influence its operations (such as filtering for noise, adjusting displays for brightness detection, applying a flash for a camera, or other features).

In one embodiment, device 900 includes power management 950 that manages battery power usage, charging of the battery, and features related to power saving operation. Power management 950 manages power from power source 952, which provides power to the components of system 900. In one embodiment, power source 952 includes an AC to DC (alternating current to direct current) adapter to plug into a wall outlet. Such AC power can be renewable energy (e.g., solar power). In one embodiment, power source 952 includes only DC power, which can be provided by a DC power source, such as an external AC to DC converter. In one embodiment, power source 952 includes wireless charging hardware to charge via proximity to a charging field. In one embodiment, power source 952 can include an internal battery or fuel cell source.

Memory subsystem 960 includes memory device(s) 962 for storing information in device 900. Memory subsystem 960 can include nonvolatile (state does not change if power to the memory device is interrupted) and/or volatile (state is indeterminate if power to the memory device is interrupted) memory devices. Memory 960 can store application data, user data, music, photos, documents, or other data, as well as system data (whether long-term or temporary) related to the execution of the applications and functions of system 900. In one embodiment, memory subsystem 960 includes memory controller 964 (which could also be considered part of the control of system 900, and could potentially be considered part of processor 910). Memory controller 964 includes a scheduler to generate and issue commands to memory device 962.

Connectivity 970 includes hardware devices (e.g., wireless and/or wired connectors and communication hardware) and software components (e.g., drivers, protocol stacks) to enable device 900 to communicate with external devices. The external device could be separate devices, such as other computing devices, wireless access points or base stations, as well as peripherals such as headsets, printers, or other devices. In one embodiment, system 900 exchanges data with an external device for storage in memory and/or for display on a display device. The exchanged data can include data to be stored in memory and/or data already stored in memory, to read, write, or edit data.

Connectivity 970 can include multiple different types of connectivity. To generalize, device 900 is illustrated with cellular connectivity 972 and wireless connectivity 974. Cellular connectivity 972 refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, LTE (long term evolution—also referred to as "4G"), or other cellular service standards. Wireless connectivity 974 refers to wireless connectivity that is not cellular, and can include personal area networks (such as Bluetooth), local area networks (such as WiFi), and/or wide area networks (such as WiMax), or other wireless communication. Wireless communication refers to transfer of data through the use of modulated electromagnetic radiation through a non-solid medium. Wired communication occurs through a solid communication medium.

Peripheral connections 980 include hardware interfaces and connectors, as well as software components (e.g., drivers, protocol stacks) to make peripheral connections. It will be understood that device 900 could both be a peripheral device ("to" 982) to other computing devices, as well as have peripheral devices ("from" 984) connected to it. Device 900 commonly has a "docking" connector to connect to other computing devices for purposes such as managing (e.g., downloading and/or uploading, changing, synchronizing) content on device 900. Additionally, a docking connector can allow device 900 to connect to certain peripherals that allow device 900 to control content output, for example, to audiovisual or other systems.

In addition to a proprietary docking connector or other proprietary connection hardware, device 900 can make peripheral connections 980 via common or standards-based connectors. Common types can include a Universal Serial Bus (USB) connector (which can include any of a number of different hardware interfaces), DisplayPort including MiniDisplayPort (MDP), High Definition Multimedia Interface (HDMI), Firewire, or other type.

In one embodiment, system 900 includes an interface to PPG sensor 990. In one embodiment, PPG sensor 990 couples directly to processor 910. In one embodiment, PPG sensor 990 couples to processor 910 via connectivity 970, peripheral connections 980, or other connection of system

900. PPG sensor 990 generates sparse measurement matrix data samples in accordance with any embodiment described herein. PPG sensor 990 measures data in accordance with a fixed pattern. The pattern can be non-uniform. The pattern can be a binary progression sequence. The sensor transmits the measurement data to processor 910 for PPG signal recovery based on compressive sensing reconstruction computations. System 900 can operate as a gateway device to perform the computations based on the sparse matrix. In one embodiment, processor 910 performs zero padding of the measurement data from PPG sensor 990.

In one aspect, a pulse oximeter system includes: a light emitting diode (LED) to emit light pulses for a photoplethysmogram (PPG) measurement; a photodetector to generate measurements based on detection of light interference of the LED light pulses with a subject; and an interface circuit to control toggling of the light pulses for the LED in accordance with a fixed schedule to cause the photodetector to generate measurements for PPG signal reconstruction based on compressive sensing of the fixed schedule light pulses.

In one embodiment, the fixed schedule capable to be selectable to generate different numbers of samples for different subjects, and the interface circuit to be preconfigured with a selected fixed schedule. In one embodiment, the interface circuit is to control toggling of the light pulses including toggle the LED light pulses in accordance with a binary based geometric progression schedule based on the subject. In one embodiment, the interface circuit is to toggle the LED light pulses in accordance with the same binary based geometric progression for every sampling window sampled by the photodetector. In one embodiment, the PPG signal reconstruction further comprises a signal processor to represent the fixed schedule as a sparse measurement matrix. In one embodiment, the PPG signal reconstruction further comprises a signal processor to perform reconstruction based on a discrete Fourier transform sparse basis representation. In one embodiment, the PPG signal reconstruction further comprises a signal processor to perform reconstruction based on a discrete cosine transform sparse basis representation. In one embodiment, the PPG signal reconstruction further comprises a signal processor to perform an L1-norm recovery based on a sparse basis representation. In one embodiment, the PPG signal reconstruction further comprises a signal processor to perform zero padding of a sparse measurement matrix prior to performance of the L1-norm recovery. In one embodiment, further comprising a processor coupled to the interface circuit, the processor to perform the PPG signal reconstruction. In one embodiment, the pulse oximeter circuit comprises a circuit on a sensor device, and further comprising a processor on a gateway device separate from the sensor device, wherein the sensor device and the gateway device communicatively coupled together. In one embodiment, the sensor circuit further comprising a communication circuit to pass raw measurement data to the gateway device from the photodetector for the gateway device to perform PPG signal reconstruction. In one embodiment, the gateway device comprises a mobile computing device.

In one aspect, a pulse oximeter circuit includes: a driver to couple to a light emitting diode (LED), and cause the LED to emit light pulses for photoplethysmogram (PPG) measurement, including to control toggling of the light pulses in accordance with a fixed schedule; and an analog to digital converter (ADC) to couple to a photodetector to generate a series of digital measurement data based on detection by the photodetector of light interference of the LED light pulses with a subject; wherein the photodetector to generate the series of digital measurement data in accordance with the fixed schedule, and the series of digital measurement data for compressive sensing reconstruction of a PPG signal.

In one embodiment, the fixed schedule capable to be selectable to generate different numbers of samples for different subjects, and the interface circuit to be preconfigured with a selected fixed schedule. In one embodiment, the driver to control toggling of the light pulses including toggle the LED light pulses in accordance with a binary based geometric progression schedule based on the subject. In one embodiment, the interface circuit is to toggle the LED light pulses in accordance with the same binary based geometric progression for every sampling window sampled by the photodetector. In one embodiment, the PPG signal reconstruction further comprises a signal processor to represent the fixed schedule as a sparse measurement matrix. In one embodiment, the PPG signal reconstruction further comprises a signal processor to perform reconstruction based on a discrete Fourier transform sparse basis representation. In one embodiment, the PPG signal reconstruction further comprises a signal processor to perform reconstruction based on a discrete cosine transform sparse basis representation. In one embodiment, the compressive sensing reconstruction of the PPG signal further comprises an L1-norm recovery based on a sparse basis representation of the PPG signal. In one embodiment, the compressive sensing reconstruction of the PPG signal further comprises zero padding a measurement matrix prior to performance of the L1-norm recovery. In one embodiment, further comprising a transmitter to send the series of measurement data to a processor to perform the compressive sensing reconstruction of the PPG signal, wherein the processor is located in a separate circuit device from the driver, ADC, and transmitter. In one embodiment, further comprising a processor coupled to the interface circuit, the processor to perform the PPG signal reconstruction. In one embodiment, the sensor circuit further comprising a communication circuit to pass raw measurement data to the gateway device from the photodetector for the gateway device to perform PPG signal reconstruction. In one embodiment, the gateway device comprises a mobile computing device.

In one aspect, a method for photoplethysmogram (PPG) measurement, comprising: toggling a light emitting diode (LED) in accordance with a fixed schedule to cause the LED to emit light pulses to a subject for PPG measurement; measuring light interference of the LED light pulses with the subject; generating a series of measurement data corresponding to the fixed schedule, the series of measurements corresponding to entries in a sparse sample matrix; transmitting the series of measurements for compressive sensing reconstruction of a PPG signal. In one embodiment, toggling the LED in accordance with the fixed schedule comprises toggling the LED in accordance with a selectable fixed schedule, preconfigured to generate different numbers of samples for different subjects. In one embodiment, toggling the LED in accordance with the fixed schedule comprises toggling the LED in accordance with a binary based geometric progression. In one embodiment, toggling the LED in accordance with a binary based geometric progression comprises applying the same binary based geometric progression for every sampling window. In one embodiment, transmitting the series of measurements comprises sending the series of measurements to a signal processor to represent the fixed schedule as a sparse measurement matrix. In one embodiment, transmitting the series of measurements comprises a sending the series of measurements to a signal processor to perform reconstruction based on a discrete Fourier transform sparse basis representation. In one embodiment, transmitting the series of measurements comprises a sending the series of measurements to a signal processor to perform reconstruction based on a discrete cosine transform sparse basis representation. In one embodiment, transmitting the series of measurements further comprises transmitting a sparse sample matrix to a processor for an L1-norm recovery based on a sparse basis representation of the PPG signal. In one embodiment, further comprising zero padding the sparse sampling matrix prior to performance of the L1-norm recovery. In one embodiment, transmitting the sparse sample matrix for compressive sensing reconstruction of the PPG signal further comprises transmitting the sparse sample matrix to a processor located in a separate circuit device. In one embodiment, transmitting the series of measurements further comprises transmitting raw measurement data to the separate circuit device. In one embodiment, the separate circuit device comprises a mobile computing device.

In one aspect, an article of manufacture comprising a computer readable storage medium having content stored thereon to cause execution of operations to execute a method for photoplethysmogram (PPG) measurement in accordance with any embodiment of the aspect of the above method. In one aspect, an apparatus for photoplethysmogram (PPG) measurement includes means for performing operations to execute a method in accordance with any embodiment of the aspect of the above method.

Flow diagrams as illustrated herein provide examples of sequences of various process actions. The flow diagrams can indicate operations to be executed by a software or firmware routine, as well as physical operations. In one embodiment, a flow diagram can illustrate the state of a finite state machine (FSM), which can be implemented in hardware and/or software. Although shown in a particular sequence or order, unless otherwise specified, the order of the actions can be modified. Thus, the illustrated embodiments should be understood only as an example, and the process can be performed in a different order, and some actions can be performed in parallel. Additionally, one or more actions can be omitted in various embodiments; thus, not all actions are required in every embodiment. Other process flows are possible.

To the extent various operations or functions are described herein, they can be described or defined as software code, instructions, configuration, and/or data. The content can be directly executable ("object" or "executable" form), source code, or difference code ("delta" or "patch" code). The software content of the embodiments described herein can be provided via an article of manufacture with the content stored thereon, or via a method of operating a communication interface to send data via the communication interface. A machine readable storage medium can cause a machine to perform the functions or operations described, and includes any mechanism that stores information in a form accessible by a machine (e.g., computing device, electronic system, etc.), such as recordable/non-recordable media (e.g., read only memory (ROM), random access memory (RAM), magnetic disk storage media, optical storage media, flash memory devices, etc.). A communication interface includes any mechanism that interfaces to any of a hardwired, wireless, optical, etc., medium to communicate to another device, such as a memory bus interface, a processor bus interface, an Internet connection, a disk controller, etc. The communication interface can be configured by providing configuration parameters and/or sending signals to prepare the communication interface to provide a data signal describing the software content. The communication interface can be accessed via one or more commands or signals sent to the communication interface.

Various components described herein can be a means for performing the operations or functions described. Each component described herein includes software, hardware, or a combination of these. The components can be implemented as software modules, hardware modules, special-purpose hardware (e.g., application specific hardware, application specific integrated circuits (ASICs), digital signal processors (DSPs), etc.), embedded controllers, hardwired circuitry, etc.

Besides what is described herein, various modifications can be made to the disclosed embodiments and implementations of the invention without departing from their scope. Therefore, the illustrations and examples herein should be construed in an illustrative, and not a restrictive sense. The scope of the invention should be measured solely by reference to the claims that follow.

What is claimed is:
1. A pulse oximeter system, comprising:
a light emitting diode (LED) to emit light pulses;
a photodetector to generate photoplethysmogram (PPG) samples based on detection of light interference of the LED light pulses with a subject; and
an interface circuit to control toggling of the light pulses from the LED to the subject, to cause the LED to toggle on a fixed schedule to cause the photodetector to generate non-uniformly spaced PPG samples with low sample coherence for PPG signal reconstruction based on compressive sensing of the light pulses, wherein the fixed schedule is selectable to generate different numbers of samples for different subjects, and the interface circuit to be preconfigured with a selected fixed schedule, including toggle the LED light pulses in accordance with a binary based geometric progression schedule based on the subject.

2. The pulse oximeter system of claim 1, wherein the interface circuit is to toggle the LED light pulses in accordance with the same binary based geometric progression for every sampling window sampled by the photodetector.

3. The pulse oximeter system of claim 1, wherein the PPG signal reconstruction further comprises a signal processor to represent the fixed schedule as a sparse measurement matrix.

4. The pulse oximeter system of claim 1, wherein the PPG signal reconstruction further comprises a signal processor to perform reconstruction based on a discrete Fourier transform sparse basis representation.

5. The pulse oximeter system of claim 1, wherein the PPG signal reconstruction further comprises a signal processor to perform reconstruction based on a discrete cosine transform sparse basis representation.

6. The pulse oximeter system of claim 1, wherein the PPG signal reconstruction further comprises a signal processor to perform an L1-norm recovery based on a sparse basis representation.

7. The pulse oximeter system of claim 6, wherein the PPG signal reconstruction further comprises a signal processor to perform zero padding of a sparse measurement matrix prior to performance of the L1-norm recovery.

8. The pulse oximeter system of claim 1, further comprising a processor coupled to the interface circuit, the processor to perform the PPG signal reconstruction.

9. The pulse oximeter system of claim 1, wherein the pulse oximeter system comprises a circuit on a sensor device, and further comprising a processor on a gateway device separate from the sensor device, wherein the sensor device and the gateway device communicatively coupled together.

10. The pulse oximeter system of claim 9, wherein the sensor circuit further comprising a communication circuit to pass raw measurement data to the gateway device from the photodetector, the processor of the gateway device to perform PPG signal reconstruction.

11. The pulse oximeter system of claim 9, wherein the gateway device comprises a mobile computing device.

12. A pulse oximeter circuit, comprising:
a driver to couple to a light emitting diode (LED), and cause the LED to emit light pulses, including to control toggling of the light pulses on a fixed schedule, in accordance with a binary based geometric progression, with the same binary based geometric progression for every sampling window; and
an analog to digital converter (ADC) to couple to a photodetector to generate a series of digital photoplethysmogram (PPG) sample data with non-uniformly spaced samples with low sample coherence based on detection by the photodetector of light interference of the LED light pulses with a subject;
wherein the photodetector to generate the series of digital sample data in accordance with the fixed schedule, and transmit the series of digital sample data for compressive sensing reconstruction of a PPG signal.

13. The pulse oximeter circuit of claim 12, wherein the compressive sensing reconstruction of the PPG signal further comprises an L1-norm recovery based on a sparse basis representation of the PPG signal.

14. The pulse oximeter circuit of claim 13, wherein the compressive sensing reconstruction of the PPG signal further comprises zero padding a measurement matrix prior to performance of the L1-norm recovery.

15. The pulse oximeter circuit of claim 12, further comprising a transmitter to send the series of sample data to a processor to perform the compressive sensing reconstruction of the PPG signal, wherein the processor is located in a separate circuit device from the driver, ADC, and transmitter.

16. A method for photoplethysmogram (PPG) measurement, comprising:
toggling a light emitting diode (LED) to cause the LED to emit light pulses on a fixed schedule in a binary based geometric progression to a subject;
measuring light interference of the LED light pulses with the subject;
generating a series of PPG samples with non-uniformly spaced samples with low sample coherence corresponding to the fixed schedule, the series of samples corresponding to entries in a sparse sample matrix;
transmitting the series of measurements for compressive sensing reconstruction of a PPG signal.

17. The method of claim 16, wherein toggling the LED in accordance with a binary based geometric progression comprises applying the same binary based geometric progression for every sampling window.

18. The method of claim 16, wherein transmitting the sparse sample matrix for compressive sensing reconstruction of the PPG signal further comprises transmitting the sparse sample matrix to a processor for an L1-norm recovery based on a sparse basis representation of the PPG signal.

19. The method of claim 18, further comprising zero padding the sparse sampling matrix prior to performance of the L1-norm recovery.

20. The method of claim 16, wherein transmitting the sparse sample matrix for compressive sensing reconstruction of the PPG signal further comprises transmitting the sparse sample matrix to a processor located in a separate circuit device.

* * * * *